(12) United States Patent
Watanabe et al.

(10) Patent No.: US 6,734,198 B1
(45) Date of Patent: May 11, 2004

(54) NEMATICIDAL TRIFLUOROBUTENES

(75) Inventors: Yukiyoshi Watanabe, Tochigi (JP); Koichi Ishikawa, Tochigi (JP); Yuichi Otsu, Tochigi (JP); Katsuhiko Shibuya, Tochigi (JP); Takahisa Abe, Hokkaido (JP)

(73) Assignee: Nihon Bayer Agrochem K.K., Tokyo (JP)

( * ) Notice: Subject to any disclaimer, the term of this patent is extended or adjusted under 35 U.S.C. 154(b) by 0 days.

(21) Appl. No.: 10/030,361

(22) PCT Filed: Jun. 28, 2000

(86) PCT No.: PCT/IB00/00868
§ 371 (c)(1),
(2), (4) Date: Mar. 5, 2002

(87) PCT Pub. No.: WO01/02378
PCT Pub. Date: Jan. 11, 2001

(30) Foreign Application Priority Data

Jul. 6, 1999 (JP) .......................................... 11-191638

(51) Int. Cl.$^7$ ........................ A01N 43/78; C07D 277/36
(52) U.S. Cl. ........................ 514/369; 548/182; 548/186
(58) Field of Search ................................ 548/182, 186; 514/369

(56) References Cited

U.S. PATENT DOCUMENTS 3,513,172 A   5/1970   Brokke ....................... 260/302

FOREIGN PATENT DOCUMENTS

| JP | 9-176141 | 8/1997 |
| WO | 86/07590 | 12/1986 |
| WO | 95/24403 | 9/1995 |

Primary Examiner—Robert W. Ramsuer
Assistant Examiner—Kamal Saeed
(74) Attorney, Agent, or Firm—Richard E. L. Henderson; Raymon J. Harmuth

(57) ABSTRACT

The invention relates to compounds of formula (I) in which X represents halogen, and n represents 0, 1 or 2, to a process for their preparations and to their use as nematacides.

9 Claims, No Drawings

NEMATICIDAL TRIFLUOROBUTENES

The present invention relates to novel trifiluorobutenes and their use as nematicides.

U.S. Pat. No. 3,518,172 describes trifluorobutenyl compounds which have nematicidal activity. Japanese Laid-open Patent Publication (PCT) No. 500037/1988(=WO 86/07590) also describes that some kinds of polyhaloalkene compounds have nematicidal activity. Further, WO 95/24403 describes that 4,4-difluorobutenyl compounds have nematicidal activity. Japanese Laid-open Patent Application No. 176141/1997 mentions thiazole derivatives having insecticidal and araricidal activity.

There have now been found novel trifluorobutenes of the formula (I)

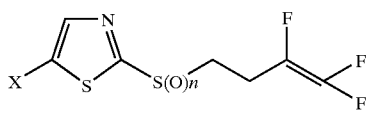

(I)

in which
X represents halogen and
n represents 0, 1 or 2.

The compounds of the formula (I) in which n represents 0 can be obtained when trifluorobutenes of the formula (Ia)

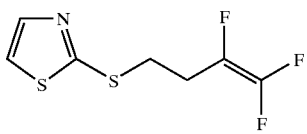

(Ia)

are reacted with a halogenating agent, optionally in the presence of one or more inert diluents (process (A)).

The compounds of the formula (I) in which
n represents 1 or 2
can be obtained when compounds of the formula (Ib)

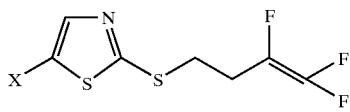

(Ib)

in which
X is the same as defined above
are reacted with an oxidizing agent, optionally in the presence of one or more inert diluents (process (B)).

The compounds of the formula (I) of the present invention have strong nematicidal activity and show good compatibility with various crops. According to the present invention the compounds of the formula (I) have surprisingly strong nematicidal activity compared with the known compounds described in the aforementioned literature.

In the present specification X preferably represents fluoro, chloro or bromo. X particularly preferably represents fluoro or chloro. X very particularly preferably represents chloro.

In the present specification n preferably represents 0 or 2. n particulary preferably represents 2.

Process (A) for preparing compounds of the formula (I) of the present invention can be represented by the following reaction scheme in which N-chlorosuccinimide is examplaryly used as halogenating agent:

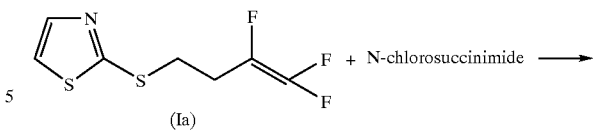

Process (B) for preparing compounds of the formula (I) of the present invention can be represented by the following reaction in which 5-chloro2-(3,4,4-trifluoro-3-butenylthio) thiazole is used as a starting material and m-chloroperoxybenzoic acid is exemplaryly used as oxidizing agent.

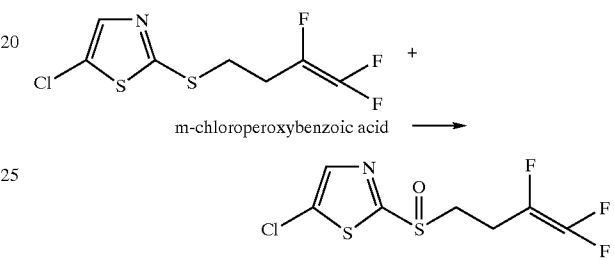

2-(3,4,4-trifluoro-3-butenylthio)thiazole is a known compound described in Japanese Laid-open Patent Publication (PCT) No. 500037/1988 (=WO 86/07590). Compounds of formula (Ib), which are used as starting material in process (B), correspond to the compounds of the formula (I) of the present invention in which n represents 0 and can be synthesized according to the aforementioned process (A).

Halogenating agents used in Process (A) can be agents usually used for this purpose in organic chemistry and which are known to a person skilled in the art, including for example sulfuryl chloride, N-chlorosuccinimide, N-bromosuccinimide, trichloro-isocyanuric acid, potassium fluoride, sodium chlorate, phosphorus pentachloride, titanium (IV) chloride, chlorine gas, bromine, iodine etc.

Oxidizing agents used for the oxidation of the above-mentioned compounds of the formula (Ib) in process (B) can be agents usually used for this purpose in organic chemistry and which are known to a person skilled in the art including for example hydrogen peroxide water, m-chloroperoxybenzoic acid, peroxyacetic acid, peroxybenzoic acid, magnesium monoperoxyphthalate, potassium peroxymonosulfate, etc.

The reaction of the above-mentioned process (A) is preferably conducted in the presence of an adequate diluent. Diluents which can be used in this process can for example be water, aliphatic, alicyclic and aromatic hydrocarbons (which can be optionally chlorinated) such as hexane, cyclohexane, petroleum ether, ligroine, benzene, methylene chloride, chloroform, carbon tetrachloride, ethylene chloride, chlorobenzene etc.; ethers, such as diethyl ether, methyl ethyl ether, di-isopropyl ether, dibutyl ether, propylene oxide, dioxane, tetrahydrofuran etc.; nitrites, such as acetonitrile, propionitrile, acrylonitrile etc.; acid amides, such as dimethylformamide, dimethylacetamide, N-methylpyrrolidone etc.; sulfones and sulfoxides, such as dimethyl sulfoxide, sulfolane etc.

The reaction temperatures of process (A) according to the invention can be varied over a relatively wide range. In general, temperatures in a range of between 0 and 200° C., preferably between 20 and 150° C. are employed. The process (A) according to the invention is generally carried out under normal pressure. However, it is possible to carry out the process (A) under elevated pressure or under reduced pressure, in general between 0.1 bar and 10 bar.

To carry out the process (A) according to the invention, the starting materials are generally employed in approximately equimolar amounts. However, it is also possible to use one of the components in a relatively large excess. Work-up is carried out according to customary methods (cf. the preparation examples).

For example, the compound of the formula (I) in which n represents 0 and X represents chloro can be obtained by reacting 1–1.2 moles of N-chlorosuccinimide with 1 mole of 2-(3,4,4-trifluoro-3-butenylthio)thiazole in carbon tetrachloride under reflux by heating.

The reaction of the above-mentioned process (B) is preferably conducted in the presence of an adequate diluent. Diluents which can be used in this process can for example be water, aliphatic, alicyclic and aromatic hydrocarbons (which can be optionally chlorinated), such as hexane, cyclohexane, petroleum, ether, ligroine, benzene, toluene, xylene, methylene chloride, chloroform, carbon tetrachloride, ethylene chloride, chlorobenzene etc.; ethers, such as diethyl ether, methyl ethyl ether, di-isopropyl ether, dibutyl ether, propylene oxide, dioxane, tetrahydrofuran etc.; nitriles, such as acetonitrile, propionitrile, acrylonitrile etc.; alcohols, for example methanol, ethanol, isopropanol, butanol, ethylene glycol etc.; esters, for example ethyl acetate, amyl acetate etc.; acid amides, for example dimethyl-formamide, dimethylacetamide, N-methylpyrrolidone etc.; sulfones and sulfoxides, for example dimethyl sulfoxide, sulfolane etc.; carboxylic acids, for example formic acid, acetic acid etc.

The reaction temperatures of process (B) according to the invention can be varied over a relatively wide range: In general, temperatures in a range of between 0 and 150° C., preferably between 0 and 120° C. are employed. The process (B) according to the invention is generally carried out under normal pressure. However, it is also possible to carry out the process (B) under elevated pressure or under reduced pressure, in general between 0.1 bar and 10 bar.

To carry out the process (B) according to the invention, the starting materials are generally employed in approximately equimolar amounts. However, it is also possible to use one of the components in a relatively large excess. Work-up is carried out according to customary methods (cf. the preparation examples).

For example, compounds of the formula (I) in which n represents 1 can be obtained by reacting, 1–2 moles of m-chloroperoxybenzoic acid with 1 mole of the compound of the formula (Ib) in methylene chloride under cooling with ice.

The compounds of the formula (I) according to the present invention show strong controlling activity against nematodes. They can, therefore, be efficiently used as nematicidal agents. The compounds of the formula (I) of the present invention do not exhibit phytotoxicity against crops and can be used for controlling harmful nematodes.

The compounds according to the invention can be used, for example, against nematodes such as Pratylenchus spp., Globodera spp., such as *Globodera rostochiensis wollenweber*, Heterodera spp., such as *Hetemodera glycines ichinohe*, Meloidogyne spp., Aphelenchoides spp., such as *Aphelenchoides basseyi christie, Radopholus similis, Ditylenchus dipsaci, Tyleachulus semipenetrans*, Longidorus spp., Xiphinema spp., Trichodorus spp., Bursaphelenchus spp., such as *Bursaphelenchus xylophilis* etc.

The compounds according to the invention are especially useful for combating Pratylenhs spp., *Globodera rostochiensis wollenweber, Heterodea glycines ichinohe*, Meloidogyne spp., *Aphelenchoides basseyi Christie, Bursaphelenchus xylophilis*.

However, the use of the active compounds according to the invention is in no way restricted to these genera, but also extends in the same manner to other nematodes.

The active compounds can be converted into the customary formulations, such as solutions, emulsions, wettable powders, water dispersible granules, suspensions, powders, dusting agents, foaming agents, pastes, soluble powders, granules, suspo-emulsion concentrates, microcapsules, fumigants, natural and synthetic materials impregnated with active compound and very fine capsules and polymeric substances.

These formulations are prepared in a known manner, for example by mixing the active compounds with extenders, that is liquid solvents, liquefied gas and/or solid diluents or carriers, if appropriate with the use of surface-active agents, that is emulsifiers and/or dispersants and/or foam-formers.

If the extender used is water, it is also possible to use, for example, organic solvents as auxiliary solvents. Suitable liquid solvents are essentially: aromatics, such as xylene, toluene, or alkylnaphthalenes, chlorinated aromatics and chlorinated aliphatic hydrocarbons, such as chlorobenzene, chloroethylenes or methylene chloride, aliphatic hydrocarbons, such as cyclohexane or paraffins, for example mineral oil fractions, mineral or vegetable oil, alcohols, such as butanol or glycol, and also their ethers and esters, ketones, such as acetone, methyl ethyl ketone, methyl isobutyl ketone or cyclobexanone, strongly polar solvents, such as dimethylformamide and dimethyl sulphoxide, and also water.

Liquefied gas diluents or carriers are liquefied substances which are gases at normal temperature and pressure. Liquefied gas diluents can be, for example, aerosol propellants such as butane, propane, nitrogen gas, carbon dioxide, halogenated hydrocarbons, etc.

Suitable solid comers are:
for example ammonium salts and ground natural minerals, such as kaolins, clays, talc, chalk, quartz, attapulgite, montmorillonite or diatomaceous earth and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut she, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.01 and 95 per cent by weight of active compound, preferably between 0.1 and 90%, particularly preferably between 0.5 and 90%.

The active compounds according to the invention, as such or in their formulations, can also be used in a mixture with known fungicides, bactericides, acaricides, nematicides or insecticides, to widen, for example, the activity spectrum or to prevent the development of resistance. In many cases, this results in synergistic effects, i.e. the activity of the mixture exceeds the activity of the individual components.

Examples of particularly advantageous mixing components are the following:

Fungicides:
- aldimorph, ampropylfos, ampropylfos potassium, andoprim, anilazine, azaconazole, azoxystrobin,
- benalaxyl, benodanil, benomyl, benzamacril, benzarnacril-isobutyl, bialaphos, binapacryl, biphenyl, bitertanol, blasticidin-S, bromuconazole, bupite, buthiobate,
- calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
- debacarb, dichlorophen, diclobutrazole, diclofluanid, diclomezine, dicloran, diethofencarb, difenoconazole, dimethirimol, dimethomorph, diniconazole, diniconazole-M, dinocap, diphenylmine, dipyrithione, ditalimfos, dithianon, dodemorph, dodine, drazoxolon,
- ediphenphos, epoxiconazole, etaconazole, ethirimol, etridiazole,
- famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, firconazole-cis, furmecyclox,
- guazatine,
- hexachlorobenzene, hexaconazole, hymexazole,
- imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
- kasugamycin, kresoxim-methyl, copper preparations, such as: copper hydroxide, copper naphthenate, copper oxychloride, copper sulphate, copper oxide, oxine-copper and Bordeaux mixture,
- mancopper, mancozeb, maneb, meferimzone, mepanipyrim, mepronil, metalaxyl, metconazole, methasulphocarb, methfuroxam, metiram, metomeclam, metsulfovax, mildiomycin, myclobutanil, myclozolin,
- nickel dimethyldithiocarbamate, nitrothal-isopropyl, nuarimol,
- ofurace, oxadixyl, oxamocarb, oxolinic acid, oxycarboxim, oxyfenthiin,
- paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quitozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol triazbutil, triazoxide, trichlamide, tricyclazole, tridamorph, triflumizole, triforine, triticonazole, uniconazole, validamycin A, vinclozolin, viniconazole, zailamide, zineb, ziram and also Dagger G,

OK-8705,

OK-8801,

α-(1,1-dimethylethy-∃-(2-phenoxyethyl)1H-1,2,4-triazole-1-ethanol,

α-(2,4-dichlorophenyl)-∃-fluoro-b-propyl-1H-1,2,4-triazole-1-ethanol,

α-(2,4-dichlorophenyl)-∃-methoxy-a-methyl-1H-1,2,4-triazole-1-ethanol,

α-(5-methyl-1,3-dioxan-5-yl)-∃-[[4(trifluoromethyl) phenyl]-methylene]-1,2,4- triazole-1 1-ethanol, (5RS,6RS)-6-hydroxy-2,2,7,7-tetramethyl-5-(1H-1,2, 4triazol-1-yl)-3-octanone, (E)-a-methoxyimino)-N-methyl-2-phenoxy-phenylacetamide, isoproyl 1-{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl) oxime, 1-(2-methyl-1-naphthalenyl)-1H-pyrrol-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluorometoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl thiocyanate, 2,6-dichloro-N-(4-tifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazol, 2-[[6-deoxy-4-O-(4-O-methyl-∃-D-glycopyranosyl)-a-D-glucopyranosyl]-amino]4-methoxy-1H-pyrrolo[2,3-d] pyrimidine-5-carbonitrile, 2-aminobutane, 2-bromo-2-(bromomethyl)-pentanedinitrile, 2-chloro-N(2,3-dihydro-1,1,3-trimethyl-1H-indene-4-yl)-3-pyrdinecarboxamide, 2-chloro-N-(2,6-dimethylphenyl)-N-(isothiocyanatomethyl)-acetamide,
2-phenylphenol (OPP),
3,4-dichloro-1-[4-(difluoromethoxy)phenyl]1H-pyrrol-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimthylethyl)N-ethyl-N-propyl-1,4-dioxaspiro[4.5]decane-2-methanamine,
8-hydroxyquinoline sulphate,
9H-xanthene-2-[(phenylamino)carbonyl]-9-carboxylic hydrazide,
bis-(1-methylethyl)3-methyl-4[(3-methylbenzoyl)-oxy]-2,5-thiophenedicarboxylate,
cis-1-(4-chlorophenyl)-2(1H-1,2,4-triazol-1-yl)-cycloheptanol,
cis-4-[3-[4-(1,1-dimethylpropyl) -phenyl-2-methylpropyl]-2,6-dimethyl-morpholine hydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6methoxy)-3-pyridinyl)-cyclopropanecarboxamide,
N-[2,2,2-trichloro-1-[(chloroacetyl)amino]-ethyl]-benzamiide,
N-[3-chloro-4,5-bis(2-propinyloxy)-phenyl]-N'-methoxy-methanimidamide,
N-formyl-N-hydroxy-DL-alanine-sodium salt,
O,O-diethyl[2-dipropylamino)-2-oxoethyl]-ethylphosphoramidothioate,
O-methyl S-phenyl phenylpropylphosphoraridothioate,
S-methyl 1,2,3-benzothiadiazole-7-carbothioate, and
spiro[2H]-1-benzopyran-2,1'(3'H)-isobenzofuran]-3'-one, Bactericides:
 bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricide/nematicides:
 abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiania, Beauveria tenella*, bendiocarb, benfuracarb, bensultap, benzoximate, betacyfluthrin, bifenazate, bifentrin, bioethanomethrin, bio-permethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, etboprophos, etofenprox, etoxazole, etrimfos, fenamiphos, fenazaquin, fenbutatin oxide, fenitrothion, fenothiocarb, fenoxacrim, fenoxycarb, fenpropatin, fenpyrad, fenpyrithrin, fenpyroximate, fenvalerate, fipronil, fluazinam, flauzuron, flubrocythrinate, flucycloxuron, flucyrnate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivemectin, nuclear polyhedrosis viruses, lambda-cyhalothrin lufenuron malathion, mecaibam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoat, oxamyl, oxydemethon M,

*Paecilomyces fumosoroseus*, parthion A, parathion M, permefirin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*

YI 5302, zeta-cypermethrin, zolaprofos, (1R-cis)-[5-(phenylmethyl)-3-furanyl]-methyl3-[(dihydro-2-oxo-3(2H)-furanlidene)-methyl]-2,2-dimethylcyclopropanecarboxylate, (3-phenoxyphenyl)-methyl2,2,3,3-tetraminethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]4,5-dihydro-oxazole, 2-(acetlyoxy)-3-dodecyl-1,4-naphthalenodione, 2-chloro-N-[[[4-(1-phenylethoxy)phenyl]amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate.

4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyndazrione, 4chloro-2-(2-chloro-2-methylpropyl)-5-[(6-iodo-3-pyridinyl)methoxy]-3(2H)-pyrdazinone, 4-chloro-5-[(6-chloro-3-pyridinyl)methoxy]-2-(3,4-dichlorophenyl)-3-(2H)-pyridazinone,

*Bacillus thuringiensis* strain EG-2348,

[2-benzoyl-1-(1,1-dimethylethyl)-hydrzinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazinie-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-diydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoroamidothioate.

A mixture with other known active compounds, such as herbicides, or with fertilizes and growth regulators is also possible.

Furthermore, when used as nematicides, the active compounds according to the invention can be present in their commercial formulations and in the use forms, prepared from these formulations, as a mixture with synergists. Synergists are compounds which increase the action of the active compounds, without it being necessary for the synergist added to be active itself.

The active-compound content of the use forms prepared from the commercial formulations can vary within wide limits. The active-compound concentration of the use forms can be from 0.0000001 to 95% by weight of active compound, preferably between 0.0001 and 1% by weight. Application is carried out in a customary manner adapted to the use forms.

The preparation and the use of the compounds according to the present invention will be described more specifically by the following examples. However, the present invention should not be restricted to them in any way. "Parts" mean "parts by weight" unless specified otherwise.

PREPARATION EXAMPLES

Example 1

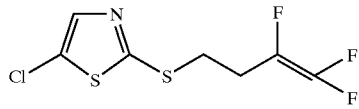

2-(3,4,4-Trifluoro-3-butenylthio)thiazole (6.75 g, 30 mM) is dissolved in carbon tetrachloride (60 ml). N-chlorosuccinimide (4.8 g) is added to the solution and refluxed for 18 hours by heating. As soon as the reaction has reached room temperature, the mixture is filtered and the solvent is distilled off. The concentrate is purified by column chromatography (eluent: hexane/ethyl acetate=90/10) to obtain 5-chloro-2-(3,4,4-trifluoro-3-butenylthio)thiazole as pale yellow liquid ($n^{20}_D$ 1.5326).

Example 2

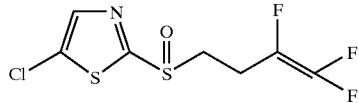

5-Chloro-2-(3,4,4-trifluoro-3-butenylthio)thiazole (2.07 g, 8 mM) is dissolved in chloroform (40 ml). m-chloroperoxybenzoic acid (1.38 g) is added to the solution under ice cooling (temperature below 4° C.) and further stirred for 8 hours at a temperature below 4° C.

10% sodium thiosulfate is added to the solution and the solution is then fractionated. The chloroform layer is washed with 5% aqueous solution of sodium hydroxide and dried over unhydrous magnesium sulfate. The solvent is distilled off and the concentrate is purified by column chromatography (eluent: hexane/ethyl acetate=90/10) to obtain 5-chloro-2-(3,4,4-trifluoro-3-butenylsulfinyl)thiazole (1.5 g) as pale yellow liquid ($n^{20}_D$ 1.5380).

Example 3

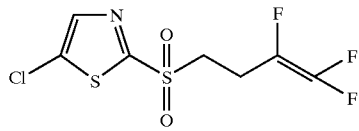

To the solution of 5-chloro-2-(3,4,4-trifuoro-3-butenylthio)thiazole (2.60 g, 10 mM) and acetic acid (28 g) 31% hydrogen peroxide water (3.29 g) is added and stirred at 55–60° C. for 6 hours. After cooling to 5° C. the reaction mixture is adjusted to pH 6 by adding an appropriate amount of an aqueous solution of sodium hydroxide, diluted with water and extracted three times with chloroform (25 ml). The chloroform layer is washed with water, 10% sodium thiosulfate and water in this order, and dried over unhydrous sodium sulfate. The solvent is distilled off and the concentrate is purified by column chromatography (eluent: hexane/ethyl acetate=90/10) to obtain 5-chloro-2-(3,4,4-trifluoro-3-butenylsulfonyl)thiazole (2.2 g) as pale yellow liquid ($n^{20}_D$ 1.5205).

REFERENCE EXAMPLE

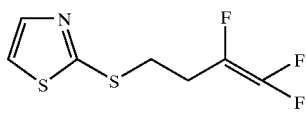

2-Mercaptothiazole (5.18 g), potassium carbonate (6.72 g) and 4-bromo-1,1,2-trifluorobutene-1 (9.21 g) are refluxed in acetonitrile (60 ml) in the presence of argon gas for 6 hours by heating. After the reaction mixture has reached room temperature, it is filtered and the solvent is distilled off. The residue is dissolved in dichloromethane and washed with 5% aqueous solution of sodium hydroxide and water in this order. It is dried over unhydrous sodium sulfate and purified by column chromatography (eluent: dichloromethane) to obtain 2-(3,4,4-trifluoro-3-butenyl-thio)thiazole (8.6 g) as pale yellow liquid ($n^{20}_D$ 1.5200).

USE EXAMPLES

Example 1

Test Against Meloidogyne spp. Soil pot Test

Preparation of Test Agent:

1 Part of the active compound is impregnated to 99 parts of pumice to obtain fine granules.

Test Method:

The test agent prepared as mentioned above was added to soil contaminated with Meloidogyne incognita to a chemical concentration of 10 ppm and homogeneously mixed by stirring. A pot (1/5000 are) was filled with the soil. About 20 seeds of tomato (variety: Kurihara) were sown per pot. After cultivation in a greenhouse for 4 weeks, they were carefully pulled out not to damage the roots and the root knot index and the controlling effect were determined as follows.

Degree of damage 0: No knots were formed (Complete control).
1: A few knots were formed.
2: Knots were formed to a medium extent.
3: Knots were formed to an intense extent.
4: Knots were formed to the most intense extent (which corresponds to non-treatment).

Root knot index =

$$\frac{\sum (\text{degree of damage} \times \text{number of individuals})}{\text{Total number of tested individuals} \times 4} \times 100$$

The controlling effect of the compounds tested can then be evaluated according to the following equation:

Controlling effect[%] =

$$\frac{\left(\begin{array}{c}\text{Root knot index at} \\ \text{non-treated area}\end{array} - \begin{array}{c}\text{Root knot index at} \\ \text{treated area}\end{array}\right)}{\text{Root knot index at non-treated area}} \times 100$$

The evaluation of the controlling effects of the compounds according to the present invention was done on the basis of the values of the controlling effect which can be obtained in the above-mentioned way and were connected with the following standards:

a: Controlling effect 100–71%
b: Controlling effect 70–50%
c: Controlling effect less than 50%
d: Controlling effect 0%

Results are shown in the following Table 1.

TABLE 1

| Compound Ex. No. | Concentration of active ingredient [ppm] | Evaluation of controlling effect |
|---|---|---|
| 1 | 10 | a |
| 2 | 10 | a |
| 3 | 10 | a |

FORMULATION EXAMPLES

Example 1

Granule

To a mixture of 10 parts of a compound according to the present invention (Example No. 1), 30 parts of bentonite (montmorillonite), 58 parts of talc and 2 parts of ligninsulphonate salt, 25 parts water are added, well kneaded, worked up into granules of 10–40 mesh with the help of an extrusion granulator and dried at 40–50° C. to obtain granules.

Example 2

Granule

95 Parts of clay mineral particles having a particle diameter distribution of 0.2–2 mm are put into a rotary mixer. While rotating it, 5 parts of a compound according to the present invention (Example No. 2) are sprayed onto the mineral particles together with a liquid diluent to obtain uniformly wetted particles and the particles are then dried at 40–50° C. to obtain granules.

Example 3

Emulsifiable Concentrates

30 Parts of a compound according to the present invention (Example No. 3), 55 parts of xylene, 8 parts of polyoxyethylene alkyl phenyl ether and 7 parts of calcium alkylbenzenesulphonate are mixed and stirred to obtain an emulsion.

Example 4

Wettable Powder 15 parts of a compound according to the present invention (Example No. 1), 80 parts of a mixture of white carbon (hydrous amorphous silicon oxide fine powders) and powder clay (1:5), 2 parts of sodium alkylbenzenesulphonate and 3 parts of sodium alkylnaphthalenesulphonate-formalin-condensate are crushed and mixed together to obtain a wettable powder.

What is claimed is:

1. A compound of the Formula (I)

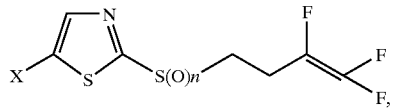

(I)

wherein

X represents halogen, and n represents 0, 1 or 2.

2. A compound of the Formula (I) according to claim 1, wherein

X represents fluoro, chloro or bromo, and n represents 0 or 2.

3. A compound of the Formula (I) according to claim 1 wherein

X represents chloro or bromo, and n represents 2.

4. A compound of the Formula (I) according to claim 1 wherein

X represents chloro.

5. A process for preparing a compound of the Formula (I)

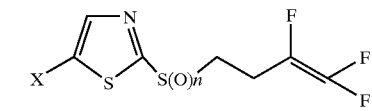

(I)

wherein

X is as defined in one of claims 1 to 4, and n represents 0, comprising the step of:

reacting 2-(3,4,4-trifluoro-3-butenylthio)thiazole with a halogenating agent, optionally in the presence of an inert solvent.

6. A process for preparing a compound of the Formula (I)

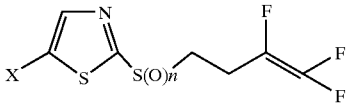

(I)

wherein n represents 1 or 2, and

X is as defined in one of claims 1 to 4, comprising the step of:

reacting a compound of the Formula (Ib)

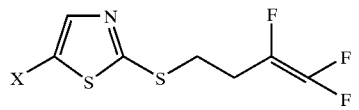

(Ib)

wherein

X is as defined in one of claims 1 to 4, with an oxidizing agent, optionally in the presence of an inert solvent.

7. A nematicidal composition comprising at least one compound of the Formula (I) according to one of claims 1 to 4.

8. A method of combating nematodes, comprising the step of allowing an effective amount of a compound of the Formula (I) according to one of claims 1 to 4 to act on a member selected from the group consisting of nematodes, a habitat of said nematodes and combinations thereof.

9. A process for preparing a nematicidal composition, comprising the step of mixing a compound of the Formula (I) according to one of claims 1 to 4 with a member selected from the group consisting of an extender a surface active agent and combinations thereof.

* * * * *